United States Patent [19]

Arhancet et al.

[11] Patent Number: 5,304,691
[45] Date of Patent: Apr. 19, 1994

[54] PROCESS FOR MAKING 1,3-PROPANEDIOL AND 3-HYDROXYPROPANAL

[75] Inventors: Juan P. Arhancet, Katy; Lynn H. Slaugh, Houston, both of Tex.

[73] Assignee: Shell Oil Company, Houston, Tex.

[21] Appl. No.: 91,108

[22] Filed: Jul. 13, 1993

[51] Int. Cl.$^5$ .................... C07C 27/20; C07C 27/00
[52] U.S. Cl. ............................... 568/867; 568/454; 568/496; 568/852
[58] Field of Search ............ 568/867, 420, 449, 496, 568/454, 852; 560/179

[56] References Cited

U.S. PATENT DOCUMENTS

| | | | |
|---|---|---|---|
| 3,401,204 | 9/1968 | Mason et al. | 260/606.5 |
| 3,456,017 | 7/1969 | Smith et al. | 260/602 |
| 3,463,819 | 8/1969 | Smith et al. | 260/602 |
| 3,527,818 | 9/1970 | Mason et al. | 260/632 |
| 4,973,741 | 11/1990 | Beavers | 560/179 |
| 5,030,766 | 7/1991 | Briggs et al. | 568/496 |
| 5,043,480 | 8/1991 | Beavers | 568/496 |

*Primary Examiner*—Werren B. Lone

[57] ABSTRACT

This invention relates to a process for making 1,3-propanediol and 3-hydroxypropanal by intimately contacting (a) ethylene oxide,
(b) tertiary phosphine-complexed cobalt carbonyl catalyst,
(c) ruthenium catalyst,
(c) carbon monoxide, and
(d) hydrogen, the molar ratio of carbon monoxide to hydrogen being from about 4:1 to about 1:6, in liquid-phase solution in an inert reaction solvent, at a temperature of from about 30° C. to about 150° C. and a pressure of from about 50 psi to about 10,000 psi.

11 Claims, No Drawings

PROCESS FOR MAKING 1,3-PROPANEDIOL AND 3-HYDROXYPROPANAL

FIELD OF THE INVENTION

This invention relates to a process for making 1,3-propanediol and 3-hydroxypropanal by hydroformylating ethylene oxide using tertiary phosphine ligand-complexed cobalt carbonyl catalysts in combination with ruthenium catalysts.

BACKGROUND OF THE INVENTION

3-Hydroxypropanal is a useful chemical intermediate. It can be readily converted to 1,3-propanediol which finds use as an intermediate in the production of polyester fibers and films.

U.S. Pat. No. 3,463,819 and No. 3,456,017 teach a process for the hydroformylation of ethylene oxide to produce 1,3-propanediol and 3-hydroxypropanal using a tertiary phosphine-modified cobalt carbonyl catalysts.

Prior art processes produce mixtures of 3-hydroxypropanal and 1,3-propanediol with 3-hydroxypropanal predominating in the mixture. It is an object of this invention to use an improved catalyst system comprising cobalt-tertiary phosphine ligand catalyst in combination with a ruthenium catalyst to hydroformylate ethylene oxide in a single step to 3-hydroxypropanal and 1,3-propanediol, with 1,3-propanediol predominating in the product.

SUMMARY OF THE INVENTION

This invention relates to a process for making 1,3-propanediol and 3-hydroxypropanal which comprises intimately contacting
(a) ethylene oxide,
(b) tertiary phosphine-complexed cobalt carbonyl catalyst
(c) ruthenium catalyst,
(c) carbon monoxide, and
(d) hydrogen, the molar ratio of carbon monoxide to hydrogen being from about 4:1 to about 1:6,
in liquid-phase solution in an inert reaction solvent, at a temperature of from about 30° C. to about 150° C. and a pressure of from about 50 psi to about 10,000 psi.

Preferably the reaction conditions are optimized to produce primarily a major amount of 1,3-propanediol and a minor amount of 3-hydroxypropanal.

Preferably the tertiary phosphine ligand is a polydentate, preferably a bidentate phosphorus ligand.

Optional acid and metal salt catalyst promoters can be utilized.

DESCRIPTION OF THE PREFERRED EMBODIMENTS

Ethylene oxide is hydroformylated by reaction with carbon monoxide and hydrogen in the presence of a catalyst system comprising a phosphine-modified cobalt carbonyl catalyst and a ruthenium catalyst. The reaction products comprise primarily 3-hydroxypropanal (and oligomers thereof) and 1,3-propanediol. The ratio of the two products can be adjusted by adjusting the amounts of catalysts present in the reaction mixture, the reaction temperature and/or the amount of hydrogen present in the reaction mixture. Preferably catalysts and conditions are optimized to provide the reaction product a major amount, i.e., 50 or more mole percent, of 1,3-propanediol and a minor amount, i.e., less than 50 mole percent, of 3-hydroxypropanal. When the term "3-hydroxypropanal" is used herein is understood to mean the monomer as well as dimers, such as 2-(2-hydroxyethyl)- 4-hydroxy-1,3-dioxane, as well as trimers and higher oligomers of 3-hydroxypropanal.

The process is conducted, in one modification, by charging the epoxide reactant, catalysts, optional catalyst promoter(s) and reaction solvent to an autoclave or similar pressure reactor and introducing the hydrogen and carbon monoxide while the reaction mixture is maintained at reaction temperature. Alternatively, the process is conducted in a continuous manner as by contacting the reactants, catalysts and optional catalyst promoter(s) during passage through a reactor which is typically tubular in form. For best results the process is conducted under conditions of elevated temperature and pressure. Reaction temperatures range from about 30° C. to about 150° C., preferably from about 50° C. to about 125° C., and most preferably from about 70° C. to about 110° C. The reaction pressure is desirably in the range of from about 50 p.s.i. to about 10,000 p.s.i., preferably from about 500 p.s.i. to about 3000 p.s.i. In one modification of the process, inert gaseous diluent is present, e.g., inert gaseous diluents such as argon, helium, methane, nitrogen and the like, in which case the reaction pressure is properly considered to be the sum of the partial pressures of the materials other than the diluent. In the preferred modification of the process, however, the reaction is conducted in the substantial absence of added diluent.

The course of the reaction is easily followed by observing the pressure decrease within the reactor, by in situ infrared absorption techniques or by periodic withdrawal and analysis of samples from the reaction system. At the conclusion of reaction, the product mixture is separated by conventional methods such as selective extraction, fractional distillation, decantation, selective crystallization and the like. The unreacted starting material as well as the catalyst and reaction solvent are suitably recycled for further reaction.

One component of the catalyst system employed in the process of the invention comprises tertiary phosphine-modified cobalt carbonyl complexes. As is discussed in greater detail hereinbelow, the tertiary phosphine complexing/stabilizing ligand portion of the cobalt catalyst complex comprises a tertiary phosphine wherein each phosphorus is completely substituted with organic substituents attached to the phosphorus by carbonphosphorus bonds.

In one modification of the process of the invention, the tertiary phosphine stabilizing ligand is a monodentate ligand, that is, the stabilizing ligand is a tertiary phosphine of a single phosphorus atom as the sole complexing site in the tertiary phosphine ligand. This class of tertiary phosphines, herein termed mono-phosphines, is generically classified as tertiary mono-phosphine of from 3 to about 60 carbon atoms wherein each phosphorus substituent is a hydrocarbon substituent, i.e., contains only atoms of carbon and hydrogen. A preferred class of tertiary mono-phosphines is represented by the formula

RRRP           (I)

wherein R independently is monovalent hydrocarbon (i.e., "hydrocarbyl") of up to 30 carbon atoms, preferably up to 20, more preferably up to 12, with the proviso that two or three Rs may together form a divalent or trivalent hydrocarbon moiety of up to 60 carbon atoms. The group R, when monovalent, is therefore alkyl, cycloalkyl or aryl of up to 30 carbon atoms, preferably of up to 12 carbon atoms, and is illustrated by alkyl R groups such as methyl, ethyl, butyl, isobutyl, 2-ethylhexyl, octyl, benzyl, 2-phenylethyl and dodecyl; by cycloalkyl R groups such as cyclopentyl, cyclohexyl, cyclooctyl, 2,3-diethylcyclopentyl, 4-butylcyclohexyl, 2,4,5-trimethylcyclohexyl and 3-butylcyclooctyl; and by aryl R groups such as phenyl, tolyl, xylyl, o-phenylphenyl, p-tert-butylphenyl, 2,4-diethylphenyl and m-cyclohexylphenyl.

An additional class of tertiary mono-phosphines comprises the class wherein two R groups together form a divalent hydrocarbon moiety. Such cyclophosphines are illustrated by 1-ethylphospholidine, 1-phenylphospholidine, 1-phenylphosphorinane, 1-butylphosphorinane, 4,4-dimethyl-1-phenylphosphorinane, 1-phenylphosphepane, 1-ethylphosphepane,3,6-dimethyl-1-phenylphosphepane, 9-phenyl-9-phosphabicyclo[4.2.1]nonane, 9-phenyl-9-phosphabicyclo[3.3.1]nonane and 9-butyl-9-phosphabicyclo[4.2.1]nonane.

In an alternate modification of the phosphine-modified cobalt complexes of the invention, the tertiary phosphine employed is a bidentate ligand, i.e., the phosphine ligand is a tertiary di-phosphine. A suitable class of tertiary di-phosphine ligands are represented by the formula

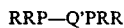  (II)

wherein R has the previously stated significance, and Q is hydrocarbylene of up to 30 carbon atoms, preferably of from 2 to 30 carbon atoms; more preferably from 2 to 20 carbons, even more preferably from 2 to 10. In a preferred embodiment Q is ethylene, propylene or butylene, more preferably ethylene. The group R, when monovalent, may be alkyl, cycloalkyl, bicycloalkyl or aryl of up to about 30 carbon atoms, preferably up to about 20 carbon atoms, more preferably of up to 12 carbon atoms, and is illustrated by alkyl R groups such as methyl, ethyl, butyl, isobutyl, 2-ethylhexyl, octyl, benzyl, 2-phenylethyl and dodecyl; by cycloalkyl R groups such as cyclopentyl, cyclohexyl, cyclooctyl, 2,3-diethylcyclopentyl, 4-butylcyclohexyl, 2,4,5-trimethylcyclohexyl and 3-butylcyclooctyl; and by aryl R groups such as phenyl, tolyl, xylyl, o-phenylphenyl, p-tertbutylphenyl, 2,4-diethylphenyl and m-cyclohexylphenyl. When two Rs on one phosphorus together form a divalent moiety, such moiety (with the phosphorus) may include 9-phosphabicyclo-[4.2.1]nonyl- and 9-phosphabicyclo[3.3.1]nonyl-. Illustrative di-phosphines of this class include 1,2-bis(diphenylphosphino)ethane, 1,2-bis(dibutylphosphino)ethane, 1,3-bis(dimethylphosphino)propane, 1,2-bis(dihexylphosphino)propane, 1,2-bis(ditolylphosphino)ethane, 1,3-bis(phenylpropylphosphino)propane, 1-(dibutylphosphino)-3-(diphenylphosphino)propane and I-(dioctylphosphino)-2-(dibutylphosphino)propane.

In an alternate modification of the phosphine-modified cobalt complexes of the invention, the tertiary phosphine employed is a polydentate ligand, i.e., the phosphine ligand is a tertiary polyphosphine represented by the formula

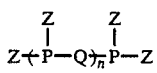  (III)

wherein Z is independently selected from R and —QP(R₂)wherein R and Q are as previously defined and n is a whole number ranging from 0 to about 10 with the proviso that at least two phosphorus atoms are present.

A particularly preferred ditertiary phosphine complexing ligand comprises a hydrocarbylene-bis(monophosphabicycloalkane) in which each phosphorus atom is joined to hydrocarbylene and is a member of a bridge linkage without being a bridgehead atom and which hydrocarbylenebis(monophosphabicycloalkane) has 11 to about 300, preferably 11 to about 200, more preferably 11 to about 100 and most preferably 18 to about 80 carbon atoms; 5 to 12, preferably 6 to 12, more preferably 7 to 12 and most preferably 8, carbon atoms thereof together with a phosphorus atom being members of each of the two bicyclic skeletal structures. Particularly preferred ditertiary phosphines are chosen from a,Z)-hydrocarbylene-P,P'-bis(monophosphabicyclononanes) in which ring systems (a) each phosphorus atom is a member of a bridge linkage, (b) each phosphorus atom is not in a bridgehead position, and (c) each phosphorus atom is not a member of the bicyclic system of the other, and (d) the smallest phosphorus-containing rings contain at least five atoms. The hydrocarbylene is preferably selected from ethylene, propylene and butylene. Most preferably the hydrocarbylene is ethylene and each of the monophosphabicyclononane moieties of the ditertiary phosphine is independently selected from 9-phosphabicyclo[4.2.1]-nonane and 9-phosphabicyclo[3.3.1]nonane. As used herein the term "9-phosphabicyclononyl" or "9-phosphabicyclononane" will refer to phosphabicyclo[4.2.1]nonane and 9-phosphabicyclo[3.3.1]nonane moieties and mixtures thereof.

In general terms the preferred ditertiary phosphine ligands used to form the cobalt-carbonyl-phosphine complexes comprise bicyclic heterocyclic ditertiary phosphines. They are hydrocarbylene-connected monophosphabicycloalkanes in which the smallest phosphorus-containing rings contain at least four, preferably at least five atoms, and the phosphorus atom therein is a member of a bridge linkage but is not a bridgehead atom. In addition to the hydrocarbylene substitution on the phosphorus atoms, the ring carbons may also be substituted. One class of such compounds has from 11 to about 300, preferably 11 to about 200, more preferably 11 to about 100 and most preferably 18 to about 80 carbon atoms, and is represented by the formula

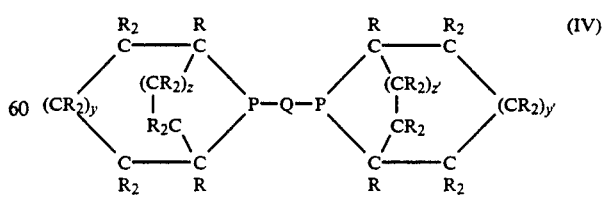  (IV)

where Q represents hydrocarbylene; R independently represents hydrogen and hydrocarbyl of 1 to about 30 carbon atoms; y and z represent zero or positive integers whose sum is from 0 to 7; y' and z', independent of the values of y and z, represent zero or positive integers whose sum is from 0 to 7; preferably y and z represent positive integers whose sum is from I to 7, more preferably from 2 to 7 and most preferably 3 with each of which having a minimum value of 1; y' and z', independent of the values of y and z, represent positive integers whose sum is from 1 to 7, more preferably from 2 to 7 and most preferably 3 with each of which having a minimum value of 1.

Hence, a preferred group of bicyclic heterocyclic ditertiary phosphines includes those represented by Formula IV where Q represents hydrocarbylene of 2 to 30 carbons and especially of 2 to 20; y and z represent positive integers whose sum is 3 and each of which has a minimum value of 1; y' and z', independent of the values of y and z, represent positive integers whose sum is 3 and each of which has a minimum value of 1; and R represents hydrogen and optionally hydrocarbyl of from 1 to 20 carbons.

The term "hydrocarbylene" is used in its accepted meaning as representing a diradical formed by removal of two hydrogen atoms from carbon atoms of a hydrocarbon or preferably one hydrogen atom from each of two different carbon atoms of a hydrocarbon. The hydrocarbylene groups represented by Q in the formula above may be any nonacetylenic acyclic or cyclic organic radical composed solely of carbon and hydrogen. Wide variation is possible in that the (nonacetylenic) acyclic or cyclic hydrocarbylene group may be arene, alkylene, alkenylene, aralkylene, cycloalkylene, straight chain, branched chain, large or small. Representative hydrocarbylene groups include ethylene, trimethylene, tetramethylene, butylene, pentamethylene, pentylene, methylpentylene, hexamethylene, hexenylene, ethylhexylene, dimethylhexylene, octamethylene, octenylene, cyclooctylene, methylcyclooctylene, dimethylcyclooctylene, isooctylene, dodecamethylene, hexadecenylene, octadecamethylene, eicosamethylene, hexacosamethylene, triacontamethylene, phenylenediethylene, and the like. A particularly useful class of bicyclic heterocyclic ditertiary phosphines is that containing only carbon, hydrogen, and phosphorus atoms. Substituted hydrocarbylene groups are also contemplated and may contain a functional group such as the carbonyl, carboxyl, nitro, amino, hydroxy (e.g. hydroxyethyl), cyano, sulfonyl, and sulfoxyl groups. A particularly useful group of ditertiary phosphines consists of those in which Q is hydrocarbylene of up to about 30 carbon atoms, preferably from 2 to 30 carbon atoms; more preferably from 2 to 20 carbons, even more preferably from 2 to 10. In a preferred embodiment Q is ethylene, propylene or butylene, more preferably ethylene.

The term "hydrocarbyl" is used in its accepted meaning as representing a radical formed by removal of one hydrogen atom from a carbon atom of a hydrocarbon. The hydrocarbyl groups represented by R in the formula above may be any nonacetylenic acyclic or cyclic organic radical composed solely of carbon and hydrogen. Wide variation is possible in that the (nonacetylenic) acyclic or cyclic hydrocarbyl group may be aryl, alkyl, alkenyl , aralkyl , cycloalkyl , straight chain, branched chain, large or small. Representative hydrocarbyl groups include methyl, ethyl, butyl, pentyl, methylpentyl, hexenyl, ethylhexyl, dimethylhexyl, octamethyl, octenyl, cyclooctyl, methylcyclooctyl, dimethylcyclooctyl, isooctyl, dodecyl, hexadecenyl, octyl, eicosyl, hexacosyl, triacontyl, phenylethyl, and the like. Substituted hydrocarbyl groups are also contemplated and may contain a functional group such as the carbonyl, carboxyl, nitro, amino, hydroxy (e.g. hydroxyethyl), cyano, sulfonyl, and sulfoxyl groups. Preferably R is hydrogen or hydrocarbyl, preferably alkyl, having 1 to about 30, preferably 1 to about 20 and most preferably from 8 to 20 carbon atoms.

Ditertiary phosphine ligands are known in the art and their method of preparation are described in detail in U.S. Pat. No. 3,401,204 and U.S. Pat. No. 3,527,818, which are both incorporated by reference herein. Other tertiary phosphine ligands are disclosed in the art, particularly the art of hydroformylation of olefins (e.g., see U.S. Pat. No. 3,448,157), and are useful in the instant process.

Generically, the tertiary phosphine-modified cobalt complexes are characterized as dicobalt hexacarbonyl complexes of additionally present tertiary phosphine ligand sufficient to provide one phosphorus complexing atom for each atom of cobalt present within the complexed molecule.

The phosphine ligands may also be partially oxidized to phosphine oxides in order to enhance the activity of the cobalt-ligand complex. The oxidation is carried out with an oxidant under mild oxidizing conditions such that an oxygen will bond to a phosphorus, but phosphorus-carbon, carbon-carbon and carbon-hydrogen bonds will not be disrupted. By suitable selection of temperatures, oxidants and oxidant concentrations such mild oxidation can occur. The oxidation of the phosphine ligands is carried out prior to the forming of the catalyst complex.

Suitable oxidizing agents include peroxy-compounds, persulfates, permanganates, perchromates and gaseous oxygen. Preferred compounds, for ease of control, are the peroxy-compounds. Peroxy-compounds are those which contain the peroxy (—O—O—) group. Suitable peroxy-compounds may be inorganic or organic. Suitable inorganic compounds include hydrogen peroxide as well as inorganic compounds which in contact with water liberate hydrogen peroxide, such compounds include the mono-valent, divalent and trivalent metal peroxides as well as hydrogen peroxide addition compounds. Also suitable are the organic peroxy-compounds, including hydroperoxides; α-oxy- and α-peroxy- hydroperoxides and peroxides; peroxides; peroxyacids; diacyl peroxides; and peroxyesters. Suitable peroxyorgano-compounds include t-butyl hydroperoxide, cumene hydroperoxide, dibenzoyl peroxide and peroxyacetic acid. Peroxy-compounds suitable for carrying out the oxidation process are known in the art, and suitable examples can be found in The Encyclopedia of Chemical Technology, Vol . 17, pp. 1–89, Third Edition (John Wiley & Sons, 1982), incorporated by reference herein.

Typically oxidation is carried out by adding to the ligand a measured amount of oxidizing agent, sufficient to carry out the degree of oxidation required. The ligand may be dissolved in a suitable solvent. The oxidizing agent is typically added slowly over a period of time to control the oxidizing conditions. The temperature is maintained to provide mild oxidizing conditions. When hydrogen peroxide is used as the oxidizing agent, the temperature is typically maintained at room temperature.

The oxidation of the ligand is carried out to provide no more than about 0.5 oxygen atoms per phosphorus atoms, on the average, in the oxidized ligand product. Preferably the ratio of oxygen atoms to phosphorus atoms in the oxidized ligand will range, on the average, from about 0.01:1 to about 0.5:1, and more preferably from about 0.05:1 to about 0.3:1.

The cobalt catalysts can be prepared by a diversity of methods. A convenient method is to combine a cobalt salt, organic or inorganic, with the desired oxidized phosphine ligand, for example, in liquid phase followed by reduction and carbonylation. Suitable cobalt salts comprise, for example, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be cobalt alkanoate of 6 to 12 carbon atoms. The valence state of the cobalt may be reduced and the cobalt-containing complex formed by heating the solution in an atmosphere of hydrogen and carbon monoxide. The reduction may be performed prior to the use of the catalysts or it may be accomplished simultaneously with the hydroformylation process in the hydroformylation zone. Alternatively, the catalysts can be prepared from a carbon monoxide complex of cobalt. For example, it is possible to start with dicobalt octacarbonyl and, by heating this substance with a suitable phosphine ligand, the ligand replaces one or more, preferably at least two, of the carbon monoxide molecules, producing the desired catalyst. When this latter method is executed in a hydrocarbon solvent, the complex may be precipitated in crystalline form by cooling the hot hydrocarbon solution. This method is very convenient for regulating the number of carbon monoxide molecules and phosphine ligand molecules in the catalyst. Thus, by increasing the proportion of phosphine ligand added to the dicobalt octacarbonyl, more of the carbon monoxide molecules are replaced.

Phosphorus:cobalt atom ratios utilized in conjunction with the catalyst complex will range from about 1:1 to about 3:1, preferably from about 1.2:1 to about 2.5:1. A ratio of about 2:1 is particularly preferred.

The optimum ratio of ethylene oxide feed to phosphine-modified cobalt carbonyl complex will in part depend upon the particular cobalt complex employed. However, molar ratios of ethylene oxide to cobalt complex from about 2:1 to about 10,000:1 are generally satisfactory, with molar ratios of from about 50:1 to about 500:1 being preferred. When batch processes are used, it is understood that the above ratios refer to the initial starting conditions.

A second component of the catalyst system employed in the process of the invention comprises a ruthenium catalyst. The ruthenium should be present in concentrations dependent upon that of the primary cobalt component. It should be present in Co:Ru atom ratio ranging from about 1000:1 to about 1:100, preferably from about 100:1 to about 1:10 and more preferably from about 50:1 to about 1:5.

The form of the ruthenium is not critical. Thus, it may be present in the form of a soluble homogeneous component or as a finely divided metal or supported on a carrier which is suspended in the reaction mixture or utilized in a fixed bed.

The soluble ruthenium components may be added in any of a number of forms including inorganic salts such as ruthenium nitrate, ruthenium sulfate, ruthenium fluoride, ruthenium chloride, ruthenium bromide, ruthenium iodide, ruthenium oxide and ruthenium phosphate or organic ruthenium salts such as ruthenium formate, ruthenium acetate, ruthenium propionate, ruthenium butyrate, ruthenium acetonylacetonate, etc., or aromatic ruthenium salts such as ruthenium benzoate, ruthenium phthalate, ruthenium naphthenate, etc., or as carbonyls such as bis-[ruthenium tricarbonyl dichloride]or bis-[ruthenium tricarbonyl dibromide], etc.

Ruthenium complexes are often more soluble than the salts and are, therefore, more desirable if high concentrations of homogeneous ruthenium solutions are desired. These complexes include ruthenium(III)-tris(2,4-pentanedionate),triruthenium dodecacarbonyl,-ruthenium(II)dichlorotris(triphenylphosphine), ruthenium(II)dichlorotetrakis-(triphenylphosphine), ruthenium(II)hydridochlorotris-(triphenylphosphine), or other soluble ruthenium complexes within the spirit of this group. Particularly suitable are ruthenium complexes of the phosphines described above which are used to form the cobalt carbonyl complexes.

The insoluble or heterogeneous ruthenium forms may be introduced as any of the forms given above which under a sufficiently hydrogen-rich atmosphere or reducing environment will give finely divided ruthenium. Alternatively, the insoluble ruthenium may be produced by reducing a soluble ruthenium form in the presence of a suitable support to give finely divided ruthenium deposited on supports including activated charcoal, alumina, silica gel, or zeolites. Other forms may be included if they can be divided finely enough by mechanical means such as ruthenium powder, ingot, shot, sponge, or wire.

The process of the invention is conducted in liquid-phase solution in an inert solvent. A variety of solvents which are inert to the reactants and catalyst and which are liquid at reaction temperature and pressure are in part operable. Illustrative of suitable solvent are hydrocarbons, particularly aromatic hydrocarbons of up to 16 carbon atoms such as benzene, toluene, xylene, ethylbenzene, and butylbenzene; alkanes such as hexanes, octanes, dodecanes, etc.; alkenes such as hexanes, octenes, dodecenes, etc.; alcohols such as t-butyl alcohol, hexanol, dodecanol, including alkoxylated alcohols; nitriles such acetonitrile, propionitrile, etc.; ketones, particularly wholly aliphatic ketones, i.e., alkanones, of up to about 16 carbon atoms such as acetone, methyl ethyl ketone, diethyl ketone, methyl isobutyl ketone, ethyl hexyl ketone and dibutyl ketone; esters of up to 16 carbon atoms, particularly lower alkyl esters of carboxylic acids which are aliphatic or aromatic carboxylic acids having one or more carboxyl groups, preferably from 1 to 2, such as ethyl acetate, methyl propionate, propyl butyrate, methyl benzoate, diethyl glutarate, diethyl phthalate and dimethyl terephthalate; and ethers of up to about 16 carbon atoms and up to 4 ether oxygen atoms, which ethers are cyclic or acyclic ethers and which are wholly aliphatic ethers, e.g., diethyl ether, diisopropyl ether, dibutyl ether, ethyl hexyl ether, methyl octyl ether, dimethoxyethane, diethylene glycol dimethyl ether, diethylene glycol diethyl ether, diethylene glycol dibutyl ether, tetraglyme, glycerol trimethyl ether, 1,2,6-trimethoxyhexane, tetrahydrofuran, 1,4-dioxane, 1,3-dioxane, 1,3-dioxolane and 2,4-dimethyl-1,3-dioxane, or which are at least partially aromatic, e.g., diphenyl ether, phenylmethyl ether, 1-methylnaphthalene, phenylisopropyl ether, halogenated hydrocarbons, such as chlorobenzene, dichlorobenzene, fluorobenzene, methyl chloride, methylene dichloride. Mixtures of solvents can also be utilized.

The amount of solvent to be employed is not critical. Typical molar ratios of reaction solvent to ethylene oxide reactant vary from about 5:1 to about 150:1.

Suitable selection of solvents can enhance product recovery. By selecting solvents with suitable polarity, a two phase system will form upon cooling of the reaction mixture with selective distribution of the catalyst and ligand in one phase and product 3-hydroxypropanal and 1,3-propanediol in a second phase. This will allow for easier separation of catalyst and ligand and recycle thereof back to the reactor. When a two phase separation process is used, solvents that would not be desirable in the reaction mixture, such as water and acids, can be used to enhance distribution of product to one phase and catalyst/ligand to the other phase.

Illustrative solvents for use in a one phase system are diethylene glycol, tetraglyme, tetrahydrofuran, t-butyl alcohol, and dodecanol. Illustrative solvents for use to provide a two phase system upon cooling are toluene, 1-methylnaphthalene, xylenes, diphenyl ether and chlorobenzene.

The process of the invention comprises contacting the ethylene oxide reactant, cobalt and ruthenium catalysts and optional catalyst promoter and with carbon monoxide and molecular hydrogen. The molar ratio of carbon monoxide to hydrogen most suitably employed is from about 4:1 to about 1:6, with best results being obtained when ratios of from about 1:1 to about 1:4 are utilized. No special precautions need to be taken with regard to the carbon monoxide and hydrogen and commercial grades of these reactants are satisfactory. The carbon monoxide and hydrogen are suitable employed as separate materials although it is frequently advantageous to employ commercial mixtures of these materials, e.g., synthesis gas.

The addition of small amounts of acids and promoting metal salts to the hydroformylation reaction mixture can further enhance or promote the conversion of ethylene oxide by increasing the activity of the catalyst. Acids are defined herein to mean those compounds which can donate a proton under reaction conditions.

Suitable acids can include inorganic acids such Hcl, Hbr, HI, boric acid and organic acids in amounts ranging from trace amounts up to about two times the molar amount of catalyst utilized. Suitable organic acids include the organs-acids having carbon numbers of 1 to about 16, such as carboxylic acids, sulfonic acids, phosphonic acids, phosphinic acids as well as other organic compounds that will donate protons under reaction conditions such as imidazole, benzoimidazole, pyridinium salts, pyrazinium salts, pyrimidinium salts, particularly salts of the aforementioned acids. Non-limiting examples of organic acids include acetic acid, propionic acid, hexanoic acid, 2-ethylhexanoic acid, octanoic acid, 3-(phenylsulfonyl)propionic acid, para-toluenesulfonic acid, 2-carboxyethylphosphonic acid, ethylphosphonic acid, n-butylphosphonic acid, t-butylphosphonic acid, phenylphosphonic acid, phenylphosphenic acid, phenyl boric acid, pyridinium para-toluenesulfonate and pyridinium octoate.

Another suitable method for providing promoter acids is to use as a catalyst precursor a cobalt salt of an organic acid, which will convert to cobalt carbonyl and the organic acid under reaction conditions. Such precursor salts include cobalt acetate, cobalt 2-ethylhexanoate, cobalt benzoate, cobalt formate and cobalt oleate. The ratio of gram equivalents of acid promoter to gram atoms of cobalt in the catalyst present in the reaction mixture will generally range from about 0.001:1 to about 4:1, preferably from about 0.01:1 to about 2:1.

Promoting amounts of metal salts can also be added to the reaction mixture along with the promoting amounts of acid to provide an even further enhanced promoting effect. Promoting amounts of one or more metal salts selected from a salt of a metal of Group IA, IIA, Group IIB, Group IIIB and the Rare Earth Series of the Periodic Table of the Elements (CAS version) are also added to the reaction mixture along with the promoting amounts of acid. Group IA comprises the alkali metals, lithium through cesium. Group IIA comprises the alkaline earth metals, calcium through barium. Group IIB comprises zinc, cadmium and mercury. Group IIIB comprises scandium, yttrium and lanthanum. The Rare Earth Group comprises cerium through lutetium. Any rqetal salt from the aforementioned Groups that is at least partially soluble in the reaction mixture is suitable. Both inorganic salts and organic salts are suitable. Included in the inorganic salts are halides, chromates, sulfates, borates, carbonates, bicarbonates, chlorates, phosphates, etc. Particularly desirable organic salts are salts of carboxylic acids having carbon numbers ranging from 1 to about 20. Examples of metal salts that have been found suitable as copromoters include halides, such as bromides, iodides, and chlorides, carboxylates, such as acetates, propionates and octoates, borates, nitrates, sulfates and the like. In general a metal salt that does not react with ethylene oxide, the reaction solvent or the hydroformylation products is suitable as copromoters with acids. The ratio of gram equivalents of metal of the salt promoter to gram atoms of cobalt in the catalyst present in the reaction mixture will generally range from about 0.001:1 to about 2:1, preferably from about 0.01:1 to about 1:1, and more preferably from about 0.1:1 to about 0.5:1.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

In the examples and tables the following definitions are used:

"1,3-PDO" is 1,3-propanediol.
"3-HPA" is 3-hydroxypropanal.

ILLUSTRATIVE EMBODIMENT I

In situ catalyst preparation and hydroformylation

EXAMPLE 1

In an inert atmosphere, a 100 ml air-stirred Parr autoclave was charged with 228 mg (0.66 mmole) of cobalt 2-ethylhexanoate, 221 mg (0.66 mmole) of 1,2-bis(9-phosphabicyclononyl)ethane (as a mixture of [4.2.1]and [3.3.1] isomers), 23 ml of dry, nitrogen-purged toluene-chlorobenzene solution (5:1 volume ratio) and 74 mg of $[Ru(CO)_3Cl_x]_2$ (0.29 remoles of ruthenium, basis metal). The autoclave was sealed and pressured to 1300 psig with a hydrogen-carbon monoxide gas mixture (4:1 molar ratio). The reaction was stirred and heated at 130° C. for 30 minutes at 1500 psig. The reactor was then cooled to an internal temperature of 5° C. and the gases were vented to leave the autoclave at ambient pressure.

Ethylene oxide (4.5 gm, 102 mmole) was added to the reactor and the reactor was then heated and stirred for 3 hours at 90° C. at a pressure of 1500 psig of hydrogen-carbon monoxide gas (1:1 molar ratio).

After cooling to 5° C., the reactor was purged with nitrogen and the two-phase product mixture was collected to give about 29 grams of solvent phase and about 2 grams of an oil phase. The two phases were independently analyzed by gas chromatography. Results are shown in Table 1 as Example 1.

COMPARATIVE EXAMPLE C-1

The above was repeated except without using the ruthenium co-catalyst. The results are shown in Table as example C-1.

EXAMPLE 2

Example 1 was repeated using sodium acetate as a promoter salt. Results are shown in Table 1 as Example 2.

EXAMPLES 3–13

Example 1 was repeated varying the promoter salt used, the phosphine ligand used and the ruthenium compound used. These variations and the results are shown in Table 1.

EXAMPLES 14–20

Example 1 was repeated using different promoter metal salts and a reaction time of 1.5 hours. Triruthenium dodecacarbonyl was used as the source of ruthenium. The results are shown in Table 2.

EXAMPLE 21

Example 1 was repeated except a 130 mg (0.42 mmoles) of 1,2-bis(9-phosphabicyclononyl)ethane (as a mixture of the [4.2.1] and [3.3.1] isomers), 17 mg (0.21 mmoles) of sodium acetate were used and 1.0 g of finely divided activated carbon having deposited on its surface 5% wt of ruthenium metal. The ethylene oxide converted was 63.2% mole and the selectivity to 3-hydroxypropanal was 5.0% mole and to 1,3-propanediol was 54.9% mole.

What is claimed is:

1. A process for making 1,3-propanediol and 3-hydroxypropanal which comprises intimately contacting
    (a) ethylene oxide,
    (b) tertiary phosphine-complexed cobalt carbonyl catalyst
    (c) ruthenium catalyst,
    (c) carbon monoxide, and

TABLE 1

| Example | Promoter[a] mmoles | Ligand[b] mmoles | Ruthenium[c] mmoles | EO Conv. Mole % | 3-HPA Mole % | 1,3-PDO Mole % |
|---|---|---|---|---|---|---|
| C-1 | 0 | LA, 0.72 | 0 | 13.0 | 100 | 0 |
| 1 | 0 | LA, 0.72 | A, 0.29 | 24.7 | 73.4 | 22.3 |
| 2 | NaOAc, 0.21 | LA, 0.72 | A, 0.29 | 58.1 | 0 | 85.7 |
| 3 | Ca(OAc)$_2$, 0.21 | LA, 0.72 | A, 0.29 | 52.8 | 18.2 | 64.8 |
| C-4 | 0 | LA, 0.72 | B, 0.29 | 52.6 | 9.7 | 84.9 |
| 4 | NaOAc, 0.21 | LA, 0.72 | B, 0.29 | 54.8 | 0 | 87.2 |
| 5 | NaOAc, 0.21 | LA, 0.72 | B, 0.15 | 54.2 | 2.9 | 83.6 |
| 6 | NaOAc, 0.21 | LA, 0.72 | B, 0.075 | 45.2 | 21.0 | 72.8 |
| 7 | NaOAc, 0.21 | LA, 0.72 | B, 0.039 | 47.2 | 66.7 | 29.0 |
| 8 | NaOAc, 0.21 | LA, 0.72 | B, 0.58 | 20.3 | 4.9 | 85.5 |
| 9 | NaOAc, 0.21 | LB, 0.72 | B, 0.29 | 49.5 | 29.6 | 36.4 |
| 10 | 0 | LB, 0.72 | B, 0.29 | 54.9 | 37.8 | 35.3 |
| 11 | NaOAc, 0.21 | LC, 0.72 | B, 0.29 | 27.2 | 37.5 | 44.2 |
| 12 | NaOAc, 0.21 | LD, 0.72 | B, 0.29 | 40.4 | 38.2 | 43.3 |
| 13 | 0 | LD, 0.72 | B, 0.29 | 58.2 | 31.3 | 49.1 |

[a]NaOAc = sodium acetate
Ca(OAc)$_2$ = calcium acetate
[b]LA = 1,2-bis(9-phosphabicyclo [4.2.1] and [3.3.1] nonyl)ethane
LB = 1,2-bis(diphenylphosphino)benzene
LC = 1,2-bis(dicyclohexylphosphino)ethane
LD = 1,2-bis(diphenylphosphino)propane
[c]In equivalents of ruthenium, basis metal:
A = [Ru(CO)$_3$Cl$_2$]$_2$
B = Ru$_3$(CO)$_{12}$

TABLE 2

| Example | Promoter[a] | EO Conv. Mole % | 3-HPA Mole % | 1,3-PDO Mole % |
|---|---|---|---|---|
| 14 | Yb(OAc)$_3$ | 59.5 | 17.5 | 76.3 |
| 15 | Eu(OAc)$_3$ | 50.8 | 17.1 | 75.0 |
| 16 | Y(OAc)$_3$ | 62.2 | 19.9 | 74.5 |
| 17 | Er(OAc)$_3$ | 53.2 | 19.3 | 73.3 |
| 18 | La(OAc)$_3$ | 39.5 | 17.6 | 74.9 |
| 19 | Zn(Oac)$_2$ | 33.0 | 4.0 | 89.2 |
| 20 | Ca(OAc)$_2$ | 30.7 | 17.8 | 74.2 |

[a]Yb(OAc)$_3$ = ytterbium acetate
Eu(OAc)$_3$ = europium acetate
Y(OAc)$_3$ = ytterbium acetate
Er(OAc)$_3$ = erbium acetate
La(OAc)$_3$ = lanthanum acetate
Zn(OAc)$_2$ = zinc acetate
Ca(OAc)$_2$ = calcium acetate (d) hydrogen, the molar ratio of carbon monoxide to hydrogen being from about 4:1 to about 1:6, in liquid-phase solution in an inert reaction solvent, at a temperature of from about 30° C. to about 150° C. and a pressure of from about 50 psi to about 10,000 psi.

2. The process of claim 1 wherein the catalyst is promoted by a promoter comprising an acid.

3. The process of claim 1 wherein the catalyst is promoted by promoter comprising a metal salt promoter selected from a salt of a metal of Group IA, Group IIA, Group IIB, Group IIIB and the Rare Earth Series of the Periodic Table of the Elements (CAS version).

4. The process of claim 3 wherein the catalyst is promoted by a promoter comprising an acid.

5. The process of claim 4 wherein the ratio of gram equivalents of acid promoter to gram atoms of cobalt in the catalyst ranges from about 0.001:1 to about 4:1 and the ratio of gram equivalents of metal of the salt promoter to gram atoms of cobalt in the catalyst ranges from about 0.001:1 to about 2:1.

6. The process of claim 1 wherein the Co:Ru atom ratio ranges from about 1000:1 to about 1:100.

7. The process of claim 6 wherein the Co:Ru atom ratio ranges from about 100:1 to about 1:10.

8. The process of claim 7 wherein the Co:Ru atom ratio ranges from about 50:1 to about 1:5.

9. The process of claim 5 wherein the Co:Ru atom ratio ranges from about 1000:1 to about 1:100.

10. The process of claim 9 wherein the Co:Ru atom ratio ranges from about 100:1 to about 1:10.

11. The process of claim 10 wherein the Co:Ru atom ratio ranges from about 50:1 to about 1:5.

* * * * *